(12) United States Patent
Kheradvar et al.

(10) Patent No.: US 9,968,446 B2
(45) Date of Patent: May 15, 2018

(54) TUBULAR SCAFFOLD FOR FABRICATION OF HEART VALVES

(71) Applicant: The Regents of the University of California, Oakland, CA (US)

(72) Inventors: Arash Kheradvar, Irvine, CA (US); Seyedhamed Alavi, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days. days.

(21) Appl. No.: 14/205,820

(22) Filed: Mar. 12, 2014

(65) Prior Publication Data

US 2014/0336755 A1 Nov. 13, 2014

Related U.S. Application Data

(63) Continuation-in-part of application No. 14/094,760, filed on Dec. 2, 2013, and a continuation-in-part of application No. 13/427,807, filed on Mar. 22, 2012, now Pat. No. 8,936,650.

(60) Provisional application No. 61/732,669, filed on Dec. 3, 2012, provisional application No. 61/466,882, filed on Mar. 23, 2011, provisional application No. 61/496,369, filed on Jun. 13, 2011, provisional
(Continued)

(51) Int. Cl.
*A61F 2/24* (2006.01)
*A61L 27/56* (2006.01)
*C12M 1/00* (2006.01)
*C12M 1/12* (2006.01)

(52) U.S. Cl.
CPC ............ *A61F 2/2415* (2013.01); *A61L 27/56* (2013.01); *C12M 23/02* (2013.01); *C12M 23/20* (2013.01); *C12M 25/14* (2013.01); *A61L 2430/20* (2013.01)

(58) Field of Classification Search
CPC .... A61F 2/2415; A61F 27/56; A61F 2430/20; C12M 23/02; C12M 25/14
See application file for complete search history.

(56) References Cited

U.S. PATENT DOCUMENTS 4,191,218 A 3/1980 Clark et al.
5,147,391 A * 9/1992 Lane ........................... 623/2.18
(Continued)

FOREIGN PATENT DOCUMENTS

EP 0781116 A1 3/1996
EP 0781116 A4 3/1996
(Continued)

OTHER PUBLICATIONS

Types of Knitted Mesh. Datasheet [online]. KnitMesh Technologies, 2009 [retrieved on Jun. 20, 2016]. Retrieved from the Internet: <URL: http://www.knitmeshtechnologies.com/manufacture-and-processing/types-of-knitted-mesh.html>.*
(Continued)

*Primary Examiner* — Kara Johnson
(74) *Attorney, Agent, or Firm* — Tope-McKay & Associates (57) ABSTRACT

A tubular braided mesh scaffold for fabrication of heart valves is described. The tubular braided scaffold can be formed of a shape memory metal, such as Nitinol, and pinched or pressed to form a leaflet shape. When heat treated, the braided mesh scaffold holds and retains its valve-like shape.

10 Claims, 6 Drawing Sheets

Related U.S. Application Data application No. 61/540,330, filed on Sep. 28, 2011, provisional application No. 61/559,694, filed on Jan. 19, 2012, provisional application No. 61/778,094, filed on Mar. 12, 2013.

(56) References Cited

U.S. PATENT DOCUMENTS

| | | | |
|---|---|---|---|
| 6,103,255 A | 8/2000 | Levene et al. | |
| 6,139,575 A | 10/2000 | Shu et al. | |
| 6,337,198 B1 | 1/2002 | Levene et al. | |
| 6,388,043 B1* | 5/2002 | Langer | B29C 61/003 525/415 |
| 6,461,382 B1 | 10/2002 | Cao | |
| 6,666,886 B1 | 12/2003 | Tranquillo et al. | |
| 6,673,109 B2* | 1/2004 | Cox | 623/2.12 |
| 6,884,621 B2 | 4/2005 | Liao et al. | |
| 7,166,464 B2 | 1/2007 | McAllister et al. | |
| 7,422,603 B2 | 9/2008 | Lane | |
| 7,521,231 B2 | 4/2009 | Germain et al. | |
| 7,575,759 B2 | 8/2009 | Murphy et al. | |
| 7,635,592 B2 | 12/2009 | West et al. | |
| 7,846,728 B2 | 12/2010 | Brooks et al. | |
| 7,851,200 B2 | 12/2010 | More | |
| 7,871,435 B2 | 1/2011 | Carpentier et al. | |
| 7,914,808 B2 | 3/2011 | Malaviya et al. | |
| 7,943,353 B2 | 5/2011 | Yu et al. | |
| 7,968,026 B1 | 6/2011 | Teoh et al. | |
| 7,972,377 B2 | 7/2011 | Lane | |
| 8,017,396 B2 | 9/2011 | Kumar et al. | |
| 8,039,258 B2 | 10/2011 | Harris et al. | |
| 8,071,007 B1 | 12/2011 | Teoh et al. | |
| 8,137,686 B2 | 3/2012 | Kladakis et al. | |
| 8,163,006 B2 | 4/2012 | Wilson et al. | |
| 8,399,243 B2 | 3/2013 | Bouten et al. | |
| 8,609,415 B2 | 12/2013 | Kortsmit et al. | |
| 2002/0094569 A1 | 7/2002 | Yu et al. | |
| 2002/0111676 A1 | 8/2002 | Bell | |
| 2002/0143393 A1* | 10/2002 | Cox | 623/2.12 |
| 2003/0027332 A1 | 2/2003 | Lafrance et al. | |
| 2004/0121459 A1 | 6/2004 | Liao et al. | |
| 2005/0002982 A1 | 1/2005 | Mooney et al. | |
| 2005/0069572 A1 | 3/2005 | Williams et al. | |
| 2005/0095711 A1 | 5/2005 | More | |
| 2005/0123520 A1 | 6/2005 | Eavey et al. | |
| 2005/0143810 A1 | 6/2005 | Dauner et al. | |
| 2005/0181016 A1 | 8/2005 | Freyman et al. | |
| 2005/0209687 A1 | 9/2005 | Sitzmann et al. | |
| 2005/0220891 A1 | 10/2005 | Yu et al. | |
| 2006/0128010 A1 | 6/2006 | Germain et al. | |
| 2006/0246584 A1 | 11/2006 | Covelli | |
| 2006/0253192 A1 | 11/2006 | Atala et al. | |
| 2006/0270028 A1 | 11/2006 | More | |
| 2006/0271166 A1 | 11/2006 | Thill et al. | |
| 2007/0041952 A1 | 2/2007 | Guilak et al. | |
| 2008/0133002 A1 | 6/2008 | Gelbart et al. | |
| 2008/0145920 A1 | 6/2008 | Bouten et al. | |
| 2009/0163612 A1 | 6/2009 | Brady et al. | |
| 2009/0222085 A1 | 9/2009 | Kumar | |
| 2009/0252795 A1 | 10/2009 | Smyth | |
| 2009/0286278 A1 | 11/2009 | Yu et al. | |
| 2010/0249922 A1 | 9/2010 | Li et al. | |
| 2011/0033885 A1 | 2/2011 | Kortsmit et al. | |
| 2012/0015331 A1 | 1/2012 | Wood et al. | |
| 2012/0244617 A1 | 9/2012 | Alavi et al. | |
| 2012/0245706 A1 | 9/2012 | Alavi et al. | |
| 2013/0217128 A1 | 8/2013 | Bouten et al. | |

FOREIGN PATENT DOCUMENTS

| | | |
|---|---|---|
| EP | 0847238 A1 | 12/1996 |
| EP | 0847238 A4 | 12/1996 |
| EP | 1406561 A2 | 1/2003 |
| EP | 1693025 A1 | 8/2006 |
| EP | 2085054 A1 | 8/2009 |
| EP | 2617389 A1 | 7/2013 |
| WO | WO/1996/008213 A1 | 3/1996 |
| WO | WO/1996/039814 A1 | 12/1996 |
| WO | 0042950 | 7/2000 |
| WO | WO/2003/007795 A2 | 1/2003 |
| WO | WO/2003/007795 A3 | 1/2003 |
| WO | WO/2003/076564 A2 | 9/2003 |
| WO | WO/2004/007699 A2 | 1/2004 |
| WO | WO/2004/018008 A1 | 3/2004 |
| WO | WO/2005/034726 A3 | 4/2005 |
| WO | WO/2005/035726 A2 | 4/2005 |
| WO | WO/2006/087101 A1 | 8/2006 |
| WO | WO/2006/099334 A2 | 9/2006 |
| WO | WO/2006/099334 A3 | 9/2006 |
| WO | WO/2003/076564 A2 | 9/2007 |
| WO | WO/2009/096780 A1 | 8/2009 |
| WO | WO 2012/181786 | 11/2012 |
| WO | WO/2013/142879 A1 | 9/2013 |

OTHER PUBLICATIONS

'Braid'. Merriam-Webster [online]. 2016, [retrieved on Jun. 20, 2016]. Retrieved from the Internet: <URL: http://www.merriam-webster.com/dictionary/braid>.*

PCT International Search Report and the Written Opinion of the International Searching Authority for PCT/US2014/024125, dated Jul. 10, 2014.

Notification of Transmittal of the International Search Report and the Written Opinion of the International Searching Authority for PCT/US2012/000159, dated Apr. 17, 2013.

Fong, P., et al., "The use of polymer based scaffolds in tissue-engineered heart valves." Progress in Pediatric Cardiology, Elsevier, Amsterdam, NL, vol. 21, No. 2, Mar. 1, 2006, pp. 193-199.

Zund, G., et al., "Tissue engineering: a new approach in cardiovascular surgery: seeding of human fibroblasts followed by human endothelial cells on resorbable mesh," European Journal of Cardia-Thoracic Surgery. No. 13, Jan. 1, 1996, pp. 160-164.

Office Action 1 for U.S. Appl. No. 13/427,807, dated Nov. 21, 2012.

Liu et al., Surface modification of titanium, titanium alloys, and related materials for biomedical applications. Materials Science and Engineering R., vol. 47, (2004), pp. 49-121.

Misfeld et al., Heart valve macro- and microstructure., Phil. Trans. R. Soc. B., vol. 362 (2007), pp. 1421-1436.

Response to Office Action 1 for U.S Appl. No. 13/427,807, dated Feb. 21, 2013.

Office Action 2 for U.S. Appl. No. 13/427,807, dated Jun. 5, 2013.

Response to Office Action 2 for U.S. Appl. No. 13/427,807, dated Sep. 5, 2013.

Office Action 3 for U.S Appl. No. 13/427,807, dated Oct. 4, 2013.

van der Merwe et al., A computational study of knitted Nitinol meshes for their prospective use as external vein reinforcement. Journal of Biomechanics, vol. 41 (2008) pp. 1302-1309.

Office Action 1 for U.S. Appl. No. 14/094,760, dated Apr. 21, 2015.

Katzer et al., Polyetheretherketane cytotoxicity and mutagenicity in vitro. Biomaterials, vol. 23 (2002) pp. 1749-1759.

Response to Office Action 1 for U.S. Appl. No. 14/094,760, dated Aug. 4, 2015.

Office Action 2 for U.S. Appl. No. 14/094,760, dated Nov. 19, 2015.

Response to Office Action 2 for U.S Appl. No. 14/094,760, dated Mar. 21, 2016.

Advisory Action for U.S. Appl. No. 14/094.760, dated Apr. 7, 2016.

Response to Advisory Action for U.S. Appl. No. 14/094,760, dated Apr. 7, 2016.

Office Action 3 for U.S. Appl. No. 14/094,760, dated Jul. 8, 2016.

PCT International Search Report PCT/US2013/072779, dated Feb. 21, 2014.

PCT Written Opinion for PCT/US2013/072779, dated Feb. 21, 2014.

d'Arcy JL, Prendergast BD, Chambers JB, Ray SG, Bridgewater B. Valvular heart disease: The next cardiac epidemic. Heart. 2011;97:91-93.

Nikomo VT, Gardin JM, Skelton TN, Gottdiener JS. Scott CG, Enriquez-Sarano M. Burden of valvular heart diseases: A population-based study. Lancet. 2006;368=1005-1011.

(56) References Cited

OTHER PUBLICATIONS

Kheradvar A, Gorman RC, Gorman JH, III, Zeeshan A, Gharib M. Evaluation of isovolumic relaxation phase in the process of ventricular remodeling following myocardial infarction. Engineering in Medicine and Biology Society, 2004. IEMBS '04. 26th Annual International Conference of the IEEE. 2004;2:3654-3657.

Shah SR VN. The effect of glycosaminoglycan stabilization on tissue buckling in bioprosthetic heart valves. Biomaterials. 2008;29:1645-1653.

Stephens EH, de Jonge N, McNeill MP, Durst CA, Grande-Allen KJ. Age-related changes in material behavior of porcine mitral and aortic valves and correlation to matrix composition. Tissue Engineering Part A. 2010;16:867-878.

Hoffmann G, Lutter, G., Cremer, J. Durability of bioprosthetic cardiac valves. Dtsch Arztebl Int. 2008;105:143-148.

Syedain ZH, Tranquillo RT. Controlled cyclic stretch bioreactor for tissue-engineered heart valves. Biomaterials. 2009;30:4078-4084.

Vesely I, Bougher D, Song T. Tissue buckling as a mechanism of bioprosthetic valve failure. Ann Thorac Surg. 1988;46:302-308.

Thubnkar M, Deck J, Aouad J. S. N., Role ofmechanical stress in calcification of aortic bioprosthetic valves. J Thorac Cardiovasc Surg. 1983;86:115-125.

Ferrans VJ, Spray TL, Billingham ME, Roberts WC. Structural changes in glutaraldehyde-treated porcine heterografts used as substitute cardiac valves: Transmission and scanning electron microscopic observations in 12 patients. Am J Cardiol. 1978;41:1159-4184.

Mendelson K, Schoen F. Heart valve tissue engineering: Concepts, approaches, progress, and challenges, Annals of Biomedical Engineering. 2006:34:1799-1819.

Breuer CK, Mettler BA, Anthony T, Sales VL, Schoen FJ, Mayer JE. Application of tissue-engineering principles toward the development of a semilunar heart valve substitute, Tissue Engineering. 2004;10:1725-1736.

Rabkin E, Schoen FJ. Cardiovascular tissue engineering. Cardiovascuiar Pathoiogy. 2002;11:305-317.

Rabkin-Aikawa E, Mayer, J.E. Jr., Schoen, F.J. Heart valve regeneration. Adv Biochem Eng Biotechnol. 2005:94:141-179.

Vesely I. Heart valve tissue engineering. Circ Res. 2005;97:743-755.

Sacks MS, Schoen FJ, Mayer JE. Bioengineering challenges for heart valve tissue engineering. Annual Review of Biomedical Engineering. 2009;11:289-313.

Shinoka T, Breuer, C.K., Tanel R.E., Zund, G., Miura, T., Ma, P.X., Langer, R., Vacanti, J.P., Mayer, J.E. Jr. Tissue engineering heart valves: Valve leaflet replacement study in a lamb model. Ann Thorac Surg. 1995,60:S513-516.

Shinoka T, Ma, P.X., Shurn-Tim, D.; Breuer, C.K., Cusick, R.A., Zund, G., Langer, R.; Vacanti, J.P., Mayer, J.E. Jr. Tissue-engineered heart valves. Autologous valve leaflet replacement study in a lamb model. Circulation. 1996;94:164-168.

Hoerstrup SP, Sodian R, Daebritz S, Wang J, Bacha EA, Martin DP, Moran AM, Guleserian KJ, Spading JS, Kaushal S, Vacanti JP, Schoen FJ, Mayer JE, Jr. Functional living trileaflet heart valves grown in vitro. Circulation. 2000;102: III-44-49.

Steinhaff G, Stock U, Karim N, Mertsching H, Timke A, Meliss RR, Pethig K, Havench A, Bader A. Tissue engineering of pulmonary heart valves on allogenic acellular matrix conduits : In vivo restoration of valve tissue. Circulation. 2000;102:III-50-55, References Cited p. 76, Principal Investigator/Program Director (Last, first, middle): Kheradvar, Arash.

van Geemen D, Riem Vis P, Soekhradj—Soechit S, Sluijter J, de Liefde—van Beast M, Kluin J, Bouten C. Decreased mechanical properties of heart valve tissue constructs cultured in platelet lysate as compared to fetal bovine serum. Tissue Engineering Part C Methods. 2011:online ahead of editing.

Grande-Allen K, Liao J. The heterogeneous biomechanics and mechanobiology of the mitral valve: Implications for tissue engineering. Current Cardiology Reports. 2011;13:113-120.

Flanagan TC, Pandit, A. Living artificial heart valve alternatives: A review. Eur Cell Mater. 2003;6:28-45.

Boontheekul T, Mooney DJ. Protein-based signaling systems in tissue engineering. Current Opinion in Biotechnology 2003;14.559-565.

Kheradvar A, Milano M, Gorman RC, Gorman JH, III, Gharib M. Estimation of elastic and viscous properties of the left ventricle based on annulus plane harmonic behavior, Conference Proceedings, Annual International Conference of the IEEE Engineering in Medicine and Biology Society (IEEE Cat., No. 06CH37748). 2006:4 pp.-4 pp. 4 pp.

Pypen CMJM, Plenk Jr H, Ebel MF, Svagera R, Wernisch J. Characterization of microblasted and reactive ion etched surfaces on the commercially pure metals niobium, tantalum and titanium. Journal of Materials Science: Materials in Medicine. 1997;8:781-784.

Oshida Y, Sachdeva R, Miyazaki S, Daly J. Effects of shot-peening on surface contact angles of biomaterials. Journal of Materials Science: Materials in Medicine. 1993;4:443-447.

Alavi SH, Kheradvar, A. Metal mesh scaffold for tissue engineering of membranes. Tissue Eng Part C. 2011: Tissue Engineering: Part C, vol. 18, No. 4, 2012, ª Mary Ann Liebert, Inc., DOI. 10,1089/ten.tec.2011.0531.

Boyan BD, Hummert T.W., Dean. D.D.. and Schwartz. Z. Role of material surfaces in regulating bone and cartilage cell responses. Biomaterials, 1996;17:137.

Kieswener K, Schwartz, Z., Hummed, T. W., and Cochran, D. L. Surface roughness modulates the local production of growth factors and Cytokines by osteoblast-like mg-63 cells, J Biomed Mater Res. 1996;32:55.

Leitao E, Barbosa MA, De Groot K. In vitro testing of surface-modified biomaterials. Journal of Materials Science: Materials in Medicine. 1998;9:543-548.

Shenton MJ, Bradley JW, van den Berg JA, Armour DG, Stevens GC. Ultralow energy ion beam surface modification of low density polyethylene. The Journal of Physical Chemistry B. 2005;109:22085-22088.

Pignataro B, Conte E, Scandurra A, Marietta G. Improved cell adhesion to ion beam-irradiated polymer surfaces. Biomaterials. 1997;18:1461-1470.

Maltz MF, Pham MT, Matz W, Reuther H, Steiner G, Richter E. Ion beam treatment of titanium surfaces for enhancing deposition of hydroxyapatite from solution. Biomolecular Engineering. 2002;19:269-272.

Kondyurin A, Pecheva E, Pramatarova L. Calcium phosphate formation on plasma immersion ion implanted low density polyethylene and polytetrafluorethylene surfaces. Journal of Materials Science: Materials in Medicine. 2008;19:1145-1153.

Gan BK, Kondyurin A, Bilek MMM. Comparison of protein surface attachment on untreated and plasma immersion ion implantation treated polystyrene: Protein islands and carpet. Langmuir. 2007;23:2741-2746.

Walachovà K, Svorcik V, Bacàkovà L, Hnatowicz V. Colonization of ion-modified polyethylene with vascular smooth muscle cells in vitro. Biomaterials. 2002;23:2989-2996.

Sugita Y, Suzuki Y, Someya K, Ogawa A, Furuhata H, Miyoshi S, Motornura T, Miyamoto H, Igo S, Nosé Y. Experimental evaluation of a new antithrombogenic stent using ion beam surface modification. Artificial Organs. 2009;33:456-463.

Appleton AJE, Appleton CTG, Boughner DR, Rogers KA. Vascular smooth muscle cells as a valvular interstitial cell surrogate in heart valve tissue engineering, Tissue Engineering Part A. 2009;15:3889-3897.

Tedder ME SA, Chen J, Liao J, Simionescu DT. Assembly and testing of stem cell-seeded layered collagen constructs for heart valve tissue engineering. Tissue Eng Part A 2010;17:25-36.

Long J, and Tranquillo, RT. Elastic fiber production in cardiovascular tissue-equivalents Matrix Biology. 2003;22339-350, References Cited p. 77, Principal Investigator/Program Director (Last, first, middle): Kheradvar, Arash.

Khaled A, and S. Durum. Lyrnphocide: Cytokines and the control of lymphoid homeostasis. Nat Rev Immunol. 2002;2:817-830.

(56) References Cited

OTHER PUBLICATIONS

Hori J, and T. Ng. Neural progenitor cells lack immunagenicity and resist destruction as allografts. Stem Cells. 2003:21-405-416.

Rabkin-Aikawa E, Farber, M., Aikawa, M., Schoen, F.J. Dynamic and reversible changes of interstitial cell phenotype during remodeling of cardiac valves. J Heart Valve Dis. 2004;13:841-847.

Aikawa E, Whittaker, P., Farber, M., Mendelson, K., Padera, R.F., Aikawa, M.. and Schoen, F.J. Human semilunar cardiac valve remodeling by activated cells from fetus to adult: Implications for postnatal adaptation. pathology, and tissue engineering. Circulation. 2006;113:1344-1352.

Wirrig EE, Hinton RB, Yutzey KE. Differential expression of cartilage and bone-related proteins in pediatric and adult diseased aortic valves. Journal of Molecular and Cellular Cardiology. 2011;50:561-569.

Liu AC, Joag VR, Gotlieb AI. The emerging role of valve interstitial cell phenotypes in regulating heart valve pathobiology. Am J Pathol. 2007;171:1407-1418.

M.S. Hahn MKM, E. Wang, R. Schmedlen, J. West. Physiologic pulsatile flow bioreactor conditioning of poly(ethytene glycol)-based tissue engineered vascular grafts. Annals of Biomedical Engineering. 2007;35:190-200.

Ku CH, P. H. Johnson, P. Batten, P. Sarathchandra, R. C. Chambers, P. M. Taylor, M. H. Yacoub, and A. H. Chester. Collagen synthesis by mesenchymal stem cells and aortic valve interstitial cells in response to mechanical stretch. Cardiovasc. Res. 2006;71,548-556.

Butcher JT, S. Tressel, T. Johnson, D. Turner, G. Sorescu, H. Jo, and R. M. Nerem. . Profiles of valvular and vascular endothelial cells reveal phenotypic differences: Influence of shear stress. Arterioscler. Thromb. Vasc. Biol. 2006;26:69-77.

Kheradvar A, Falahatpisheh, A. The effects of dynamic saddle annulus and leaflet length on transmitral flow pattern and leaflet stress of a bi-leaflet bioprosthetic mitral valve. J Heart Valve Dis. 2011; The Edwards Lifesciences Center for Advanced Cardiovascular Technology, The Henry Samueli School of Engineering, University of California, Irvine, Irvine, CA, USA, J Heart Valve Dis, vol. 21. No. 2, Mar. 2012.

Kheradvar A, Gharib M. On mitral valve dynamics and its connection to early diastolic flow. Annals of Biomedical Engineering. 2009;37:1-13.

Kheradvar A, Kasalko J, Johnson D, Gharib M. An in vitro study of changing profile heights in mitral bioprostheses and their influence on flow. Asaio Journal. 2006;52:34-38.

Hildebrant J, Fukaya. H, Martin CJ. Stress-strain relations of tissue sheets undergoing uniform twodimensional stretch. J Appl Physiol,. 1969;27:758-762.

Schenke-Layland K. Non-invasive multiphoton imaging of extracellular matrix structures. J Biophotonics. 2008;1:451-462.

Schenke-Layland K, Madershahian N, Riemann I, Starcher B, Halbhuber KJ, Konig K, Stock UA. Impact of cryopreservation on extracellular matrix structures of heart valve leaflets. Ann Thorac Surg., 2006;81:918-926.

Chen J, Lee A, Zhao J, Wang H, Lui H, McLean DI, Zeng H. Spectroscopic characterization and microscopic imaging of extracted and in situ cutaneous collagen and elastic tissue components under two-photon excitation. Skin Res Technol. 2009;15:418-426.

Cox G, Kable E, Jones A. Fraser I, Manconi F, Gorrell MD. 3-dimensional imaging of collagen using second harmonic generation. J Struct Biol. 2003;141:53-62.

Georgiou E, Theodossiou T, Hovhannisyan V, Politopoulos K, Rapti GS, Yova D. Second and third optical harmonic generation in type i collagen, by nanosecond laser irradiation, over a broad spectral region. Optics Communications. 2000;176:253-260, References Cited p. 78, Principal Investigator/Program Director (Last, first, middle): Kheradvar, Arash.

Liu WF, Ma M, Brattie KM, Deng TT, Langer R, Anderson DG. Real-time in vivo detection of biomaterial-induced reactive oxygen species. Biomaterials. 2011;32:1796-1801.

Ma M, Liu WF, Hill PS, Brattie KM, Siegwart DJ, Chin J, Park M, Guerreiro J, Anderson DG. Development of cationic polymer coatings to regulate foreign-body responses. Advanced Materials. 2011;23:H189-H194.

McGuigan AP, Sefton MV. The thrombogenicity of human umbilical vein endothelia cell seeded collagen modules. Biomaterials. 2008;29:2453-2463.

Salvador-Morales C, Zhang L, Langer R. Farokhzad DC. Immunocompatibility properties of lipid-polymer hybrid nanopartictes with heterogeneous surface functional groups. Biomaterials. 2009;30:2231-2240.

Bobak D, Frank M, Tenner A. Characterization of c1q receptor expression on human phagocytic cells: Effects of pdbu and fmlp. The Journal of Immunology. 1986;136;4604-4610.

Saidi IS, Jacques SL, Tittel FK. Mie and rayleigh modeling of visible-light scattering in neonatal skin. Appl. Opt. 1995;34:7410-7418.

Na GC, Butz LJ, Bailey DG, Carroll RJ. In vitro collagen fibril assembly in glycerol solution: Evidence for a helical cooperative mechanism involving microfibrils. Biochemistry. 1986;25:958-966.

Kuznetsova N, Chi SL. Leikin S. Sugars and polyols inhibit fibrillogenesis of type i collagen by disrupting hydrogen-bonded water bridges between the helices. Biochemistry. 1998;37:11888-11895.

Deymier-Black AC, Almer JD, Stock SR, Haeffner DR, Dunand DC. Synchrotron x-ray dirffraction study of load partitioning during elastic deformation of bovine dentin. Acta Biomater. 2010;6:2172-2180.

Yeh AT, Choi B, Nelson JS, Tromberg BJ. Reversible dissociation of collagen in tissues. 2003;121;1332-1335.

Wells PB, Yeh AT, Humphrey JD. Influence of glycerol on the mechanical reversibility and thermal damage susceptibility of collagenous tissues. IEEE Trans Biomed Eng, 2006;53:747-753.

Liu YC, Chiang AS. High-resolution confocal imaging and three-dimensional rendering. Methods, 2003;30:86-93.

Hera M, Dizon RF, Glick BS, Lee CS, Kaestner KH, Piston DW, Bindokas VP. Imaging pancreatic betacells in the intact pancreas. Am J Physiol Endocrinol Metab. 2006;290.E1041-1047.

Iijima K, Liu HP, Chiang AS, Hearn SA, Konsolaki M, Zhong Y. Dissecting the pathological effects of human abeta40 and abeta42 in *Drosophila*: A potential model for alzheimer's disease. Proc Natl Acad Sci U S A. 2004;101 6623-6628.

Kheradvar A, Milano M, Gorman R, Gorman J, Gharib M. Assessment of left ventricular viscoelastic components based on ventricular harmonic behavior. Cardiovascular Engineering. 2006;6:30-39.

Abu-Omar Y, Ratnatunga CP. Prosthetic heart valves. Surgery 26 (Oxford). 2008 Published by Elsevier Ltd., pp. 196-500.

Apte SS, Paul A, Prakash S, Shum-Tim D. "Current developments in the tissue engineering of autologous heart valves: Moving towards clinical use." Future Cardiology, 7, 2011; pp. 77-97.

Smith DB, Sacks MS, Pattany PM, Schroeder R., Fatigue-induced changes in bioprosthetic heart valve three dimensional geometry and the relation to tissue damage. J Heart Valve Dis. Jan. 1999;8(1): pp. 25-33.

Adamczyk MM, Vesely I. Biaxial strain distributions in explanted porcine bioprosthetic valves. J Heart Valve Dis. Sep. 2002;11(5): pp. 688-695.

Vesely I, Barber JE, Ratliff NB. Tissue damage and calcification may be independent mechanisms of bioprosthetic heart valve failure. J Heart Valve Dis. 2001;10: pp. 471-477.

Alavi SH, Kheradvar, A. A hybrid self-regenerative tissue approach as a proper alternative for prosthetic heart valves. ASAIO J. 2011;57: p. 88.

Alavi SH, Kheradvar, A. A hybrid self-renewal engineered tissue for heart valve leaflets. Society of Heart Valve Disease 6th Biennial Meeting. 2011.

Mulholland DL, Gotlieb, A.I. Cell biology of valvular interstitial cells. Can J Cardiol. Mar. 1996;12(3): pp. 231-236.

Tranquillo ZHSaRT. Controlled cyclic stretch bioreactor for tissue-engineered heart valves. Biomaterials 30 (2009): pp. 4078-4084.

(56) References Cited

OTHER PUBLICATIONS van den Broek CN, Pullens RAA, Frøbert O, Rutten MCM, den Hartog WF, van de Vosse FN. Medium with blood-analog mechanical properties for cardiovascular tissue culturing. Biorheology. 2008;45(6): pp. 651-661.

Zioupos P, Barbenel JC, Fisher J. Mechanical and optical anisotropy of bovine pericardium. Med Biol Eng Comput. 1992;30: pp. 76-82.

Response to Office Action 3 for U.S. Appl. No. 14/094,760, dated Dec. 8, 2016.

* cited by examiner

TUBULAR SCAFFOLD FOR FABRICATION OF HEART VALVES

CROSS-REFERENCE TO RELATED APPLICATIONS

This is a Continuation-in-Part application of U.S. application Ser. No. 14/094,760, filed on Dec. 2, 2013, entitled, "Apparatus for Growing a Heart Valve in Three-Dimensions," which is a non-provisional application of U.S. Provisional Application No. 61/732,669, filed on Dec. 3, 2012, and entitled, "Apparatus for Growing a Heart Valve in Three-Dimensions."

This is ALSO a Continuation-in-Part application of U.S. patent application Ser. No. 13/427,807, filed on Mar. 22, 2012, and entitled, "Mesh Enclosed Tissue Constructs," which is a non-provisional application of U.S. Provisional Application No. 61/466,882, entitled "A SELF-REGENERATIVE HYBRID TISSUE STRUCTURE FOR 3D FABRICATION OF HEART VALVES, BLOOD VESSELS AND OTHER CONSTRUCTS," filed on Mar. 23, 2011; AND U.S. Provisional Application No. 61/496,369, entitled, "HYBRID TISSUE ENGINEERED HEART VALVE," filed on Jun. 13, 2011; AND U.S. Provisional Application No. 61/540,330, entitled, "Scaffold for Fabrication of Engineered Heart Valves and Other Applications," filed on Sep. 28, 2011; AND U.S. Provisional Application No. 61/559,694, entitled, "METAL MESH SCAFFOLD FOR TISSUE ENGINEERING OF MEMBRANES," filed on Jan. 19, 2012.

This is ALSO a non-provisional application of U.S. Provisional Application No. 61/778,294, filed on Mar. 12, 2013, and entitled, "Tubular Braided Scaffold for Fabrication of Heart Valves."

BACKGROUND OF THE INVENTION (1) Field of Invention

The present invention relates to a heart valves and, more particularly to a tubular mesh or braided scaffold for use in fabrication of heart valves.

(2) Description of Related Art

Valvular heart disease is the next cardiac epidemic. While replacement of a dysfunctional valve markedly reduces the mortality associated with it, the current options are limited to either mechanical or bio-prosthetic heart valves. Mechanical heart valves tend to last longer due to their stronger composition, but the lifelong need for anticoagulant medication is their major drawbacks. In contrast, bio-prosthetic heart valves, including transcatheters, do not require anticoagulant medications but they do not last long, and are calcified rapidly due to the several production procedures such as cross-linking that they go through.

Thus, a continuing need exists for a long lasting and stable heart valve that is resistant to calcification and a method for making the same.

SUMMARY OF INVENTION

The present invention relates to a tubular scaffold for use in fabrication of heart valves. The tubular scaffold comprises a tubular mesh material shaped into a valvular structure having at least two leaflets.

In another aspect, the mesh material is braided, such that the tubular mesh material is a tubular braided scaffold.

In yet another aspect, the tubular scaffold is shaped into a tri-leaflet valvular structure.

In another aspect, the tubular scaffold is shaped into a hi-leaflet valvular structure.

In yet another aspect, the tubular scaffold is made of polymeric materials.

In another aspect, the tubular scaffold is made of metallic materials.

In yet another aspect, the tubular scaffold includes a leaflet portion and a tubular portion, with the leaflets formed on the leaflet portion, and wherein a shape of each leaflet corresponds to a portion of a surface of a cone which portion is defined by the intersections on the conical surface of at least two flat planes having peripheries on the conical surface corresponding in length respectively to the circumference of the base with the leaflets each having a peripheral five portion while on the other side are attached to a tubular portion.

In another aspect, the tubular mesh material shaped into a valvular structure is fitted onto a frame of an artificial heart valve. Further, the scaffold is connected to a frame having a base and at least two upstanding posts.

Finally, as can be appreciated by one in the art, the present invention also comprises a method for forming and using the invention described herein.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

The present invention relates to a heart valves and, more particularly, to a tubular braided scaffold for use in fabrication of heart valves. The following description is presented to enable one of ordinary skill, in the art to make and use the invention and to incorporate it in the context of particular applications. Various modifications, as well as a variety of uses in afferent applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is only one example of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter clockwise have been used for convenience purposes only and are not intended to imply an particular fixed direction. Instead, they are used to reflect relative locations and/or directions between various portions of an object.

(1) Description

The present invention relates to a scaffold for formation of heart valves. More specifically, the present invention relates to a valvular scaffold made of as tube that has a braided (or mesh) pattern that is shaped into a (1) tri-leaflet or (2) bi-leaflet valvular structure, where the scaffold can be made from a variety materials such as but not limited to woven polymer or metallic fibers such as Nitinol. The formed valve can be later connected to a structure such as but not limited to a tri or bi-leaflet artificial heart valve frame to become ready for implantation. The current invention can be used as a mechanical valve. Upon proper selection of the scaffold material, it can become elastic or super elastic to provide its leaflets with enough flexibility suitable for heart valve applications. This flexibility will help the valve to improve blood flow dynamics and therefore reduce the formation of blood clots due to damaging red blood cells and finally eliminate the use of anticoagulation therapy needed for patients having mechanical heart valves.

Figure 1:
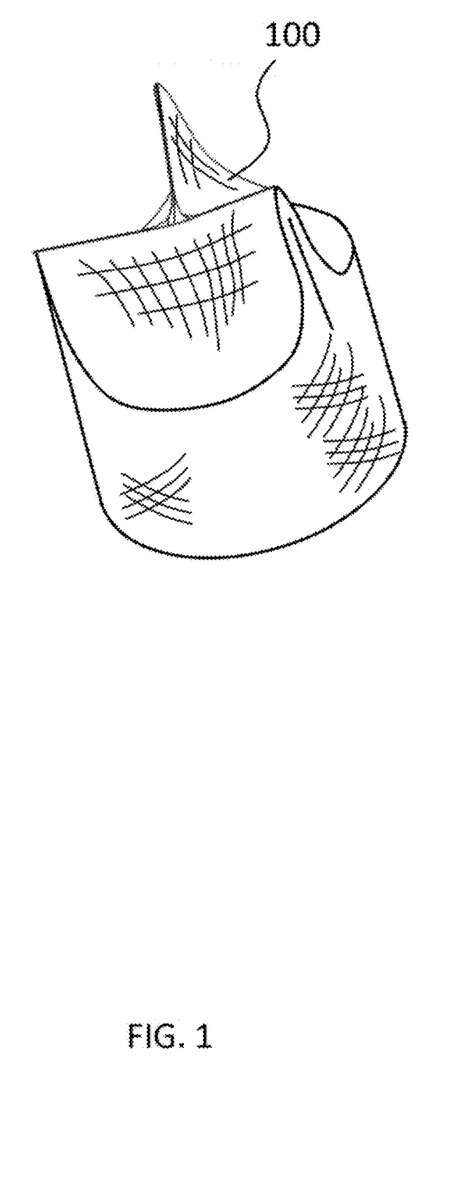
FIG. 1 is an illustration of a tubular scaffold that has been formed to a shape of a tri-leaflet heart valve.
Figure 2A:
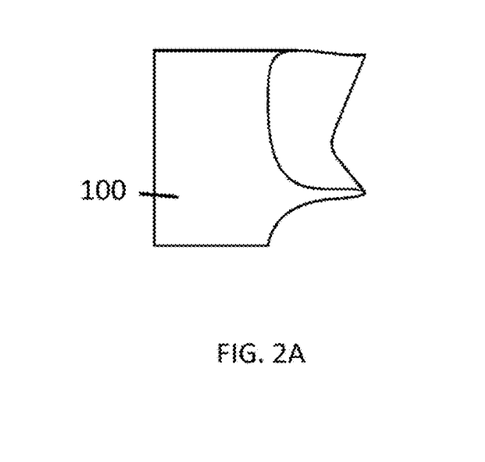
FIG. 2A is a right, side-view illustration of the tubular scaffold according to the principles of the present invention.
Figure 2B:
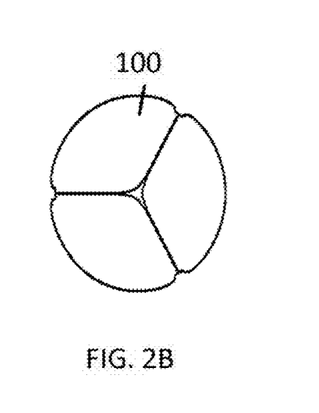
FIG. 2B is a bottom-view illustration of the tubular scaffold according to the principles of the present invention.
Figure 2C:
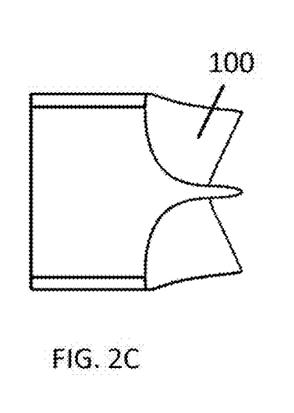
FIG. 2C is a rear, side-view illustration of the tubular scaffold according to the principles of the present invention.
Figure 2D:
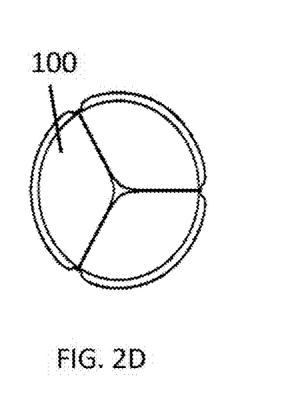
FIG. 2D is a top-view illustration of the tubular scaffold according to the principles of the present invention.

FIG. 1 shows a tubular scaffold 100 that has been formed to a shape of a tri-leaflet heart valve. For further understanding. FIGS. 2A through 2D illustrate right, bottom, rear, and top views, respectively, of the tubular scaffold 100. As shown, the scaffold 100 is a continuous mesh without any parts sewn or attached to the valve. The whole structure has integrity so that the leaflets are not separate parts from the body of the tube.

Figure 3:
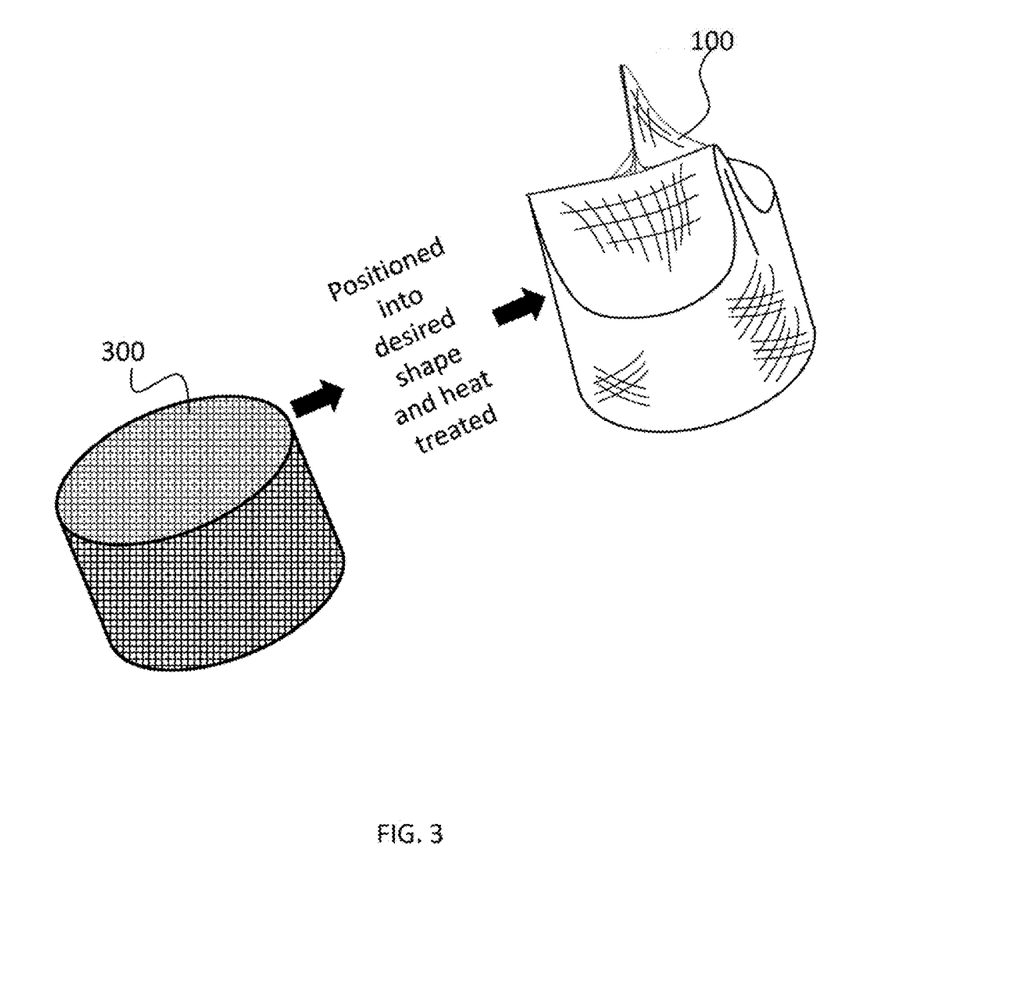
FIG. 3 is an illustration depicting an example of forming the tubular scaffold from a braided mesh tube.

The tubular scaffold 100 can be formed using any suitable mechanism or technique. As a non-limiting example, a frame (such as a bioprosthetic heart valve frame) can be used as a base mold. For example and as shown in FIG. 3, a braided mesh tube 300 can be positioned (by pinching the leaflets into shape around the base mold) and heat treated to firm a heart valve shape (i.e., the tubular scaffold 100). If the braided mesh scaffold 100 is formed of a shape memory material, such as Nitinol, then it has memory and will hold the shape as depicted in the figures.

Figure 4:
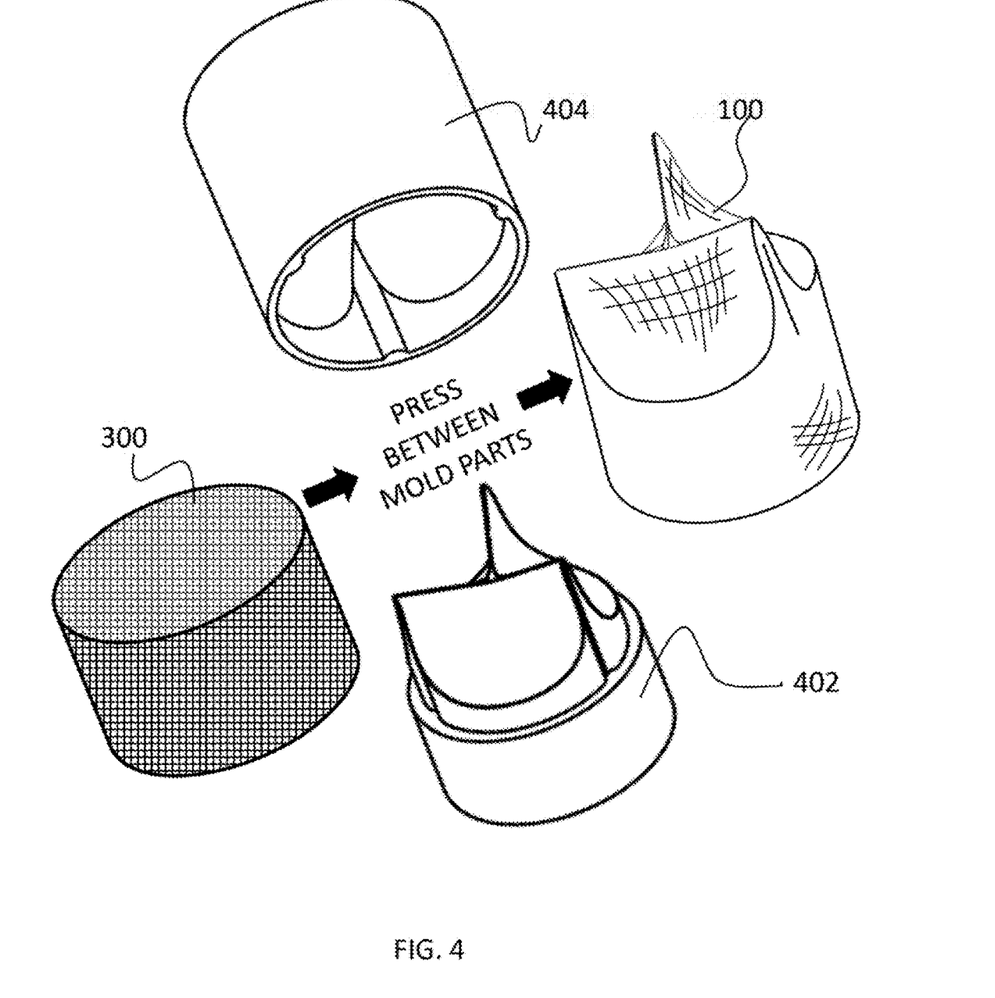
FIG. 4 is an illustration depicting a process of forming the tubular scaffold using a scaffolding mold having a scaffolding mold first part and a scaffolding mold second part according to the principles of the present invention.

As another non-limiting example and as shown FIG. 4, a scaffolding mold can be included that includes a scaffolding mold first part 402 and a scaffolding mold second part 404. The scaffolding mold second pan 404 is formed in the shape of a desired heart valve, a non-limiting example of which includes a tri-leaflet heart valve. Alternatively, the scaffolding mold second part 404 is formed to be a negative of the shape of the scaffolding, mold first part 402. Thus, when a material is positioned between the scaffolding mold first pan 402 and the scaffolding mold second part 404 is pressed over and onto the scaffolding mold first part 402, the material is pressed or bent into the desired heart valve shape, thereby creating a scaffold for use with the heart mold. As a non-limiting example and as shown in FIG. 4, a braided mesh tube 300 (e.g., made of Nitinol or any other mesh or braided material) can be positioned over the scaffolding mold first part 402. The scaffolding mold first 402 and second 404 parts are designed in a such a way that if you put the parts 402 and 404 together, there will be a uniform gap between their surfaces so that there will be enough space for the mesh 300 to be placed in between. Depending on the thickness of the mesh, the gap dimension can be adjusted.

Thus, the scaffolding mold second part 404 can be positioned over the metal braided mesh tube 300 such that the metal mesh tube 300 is pressed between the scaffolding mold first pan 402 and scaffolding mold second part 404 (i.e., the two parts 404 and 406 are compressed together). In this aspect, upon removal from the scaffolding mold, the braided mesh tube 300 is pressed into the shape of a desired scaffold 100.

Figure 5:
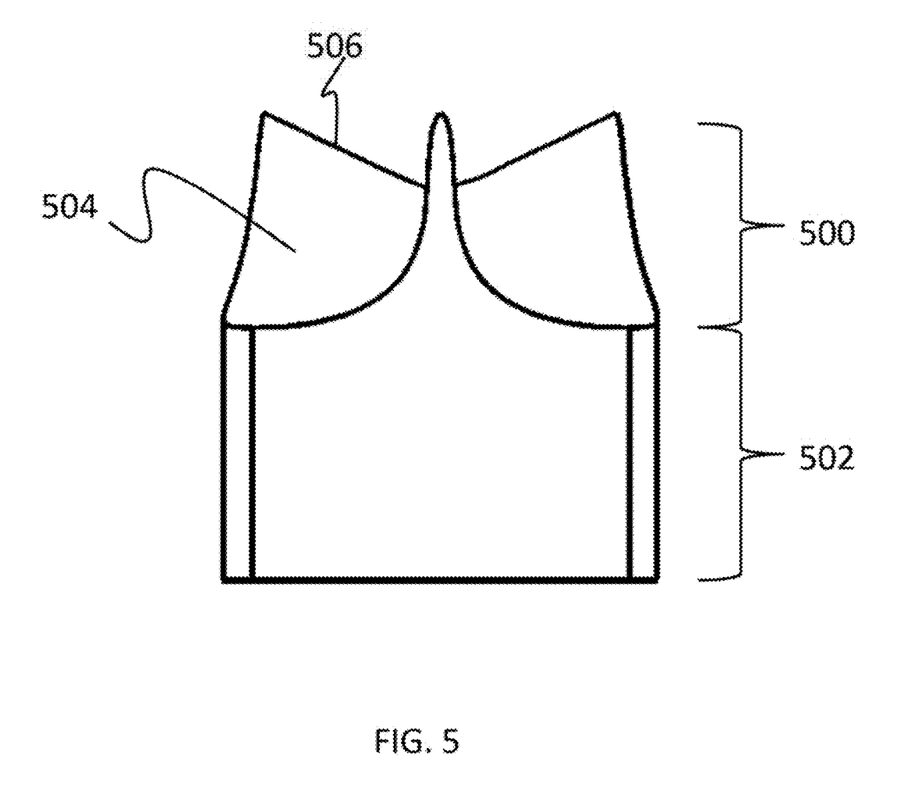
FIG. 5 is an illustration of a tubular scaffold according to the principles of the present invention.

As noted above, the tubular scaffold 100 can be formed in any desired shape having leaflets, non-limiting examples of which include having a bi-leaflet shape and a tri-leaflet shape. In another aspect and as shown in FIG. 5, the tubular scaffold 100 includes a leaflet portion 500 and a tubular portion 502, with the leaflets 504 formed on the leaflet portion 500. A shape of each leaflet 504 corresponds to a portion of a surface of a cone which portion is defined by the intersections on the conical surface of at least two flat planes having peripheries on the conical surface corresponding in length respectively to the circumference of the base with the leaflets 504 each having a peripheral free portion 506 while on the other side are attached to the tubular portion 502.

Figure 6:
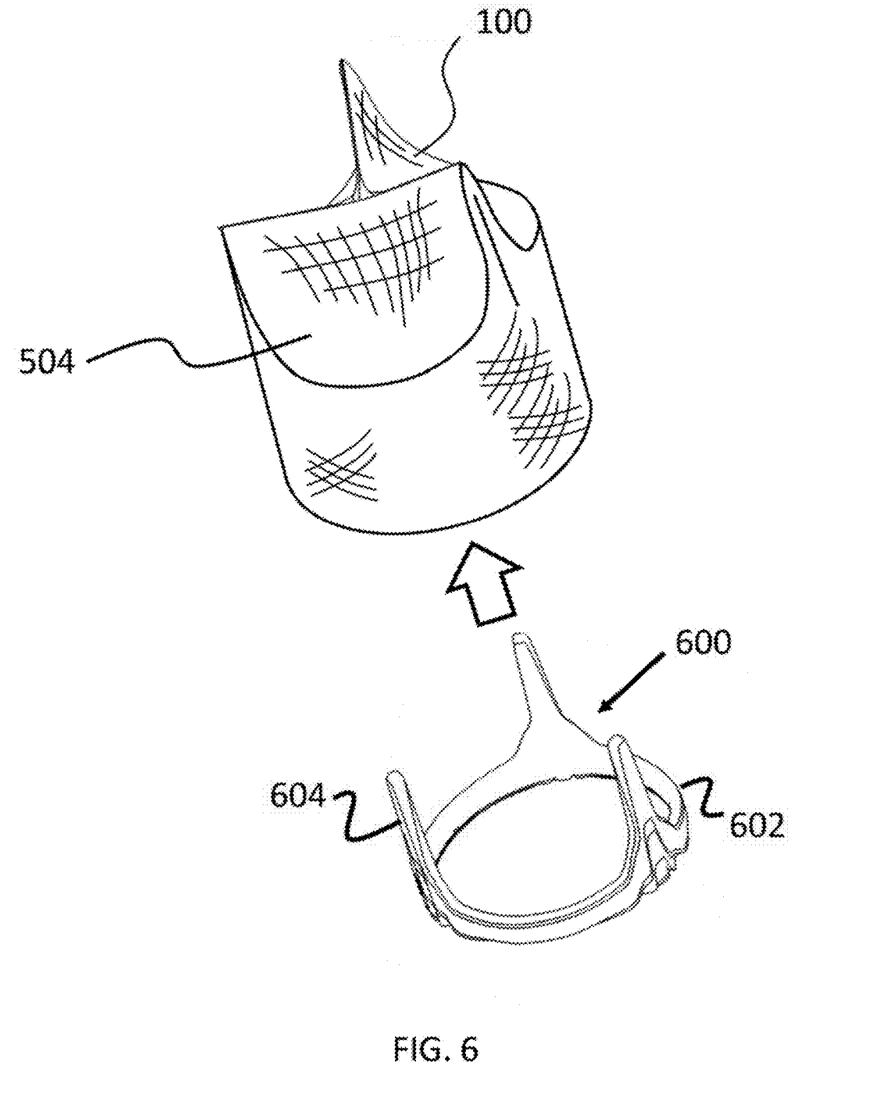
FIG. 6 is an illustration depicting a tubular scaffold as being fitted onto a frame according to the principles of the present invention.

In other aspect and as shown in FIG. 6, the tubular scaffold 100 can be attached fitted onto a frame 600 of an artificial heart valve. For example, a ring base 602 and two to three posts 604 would be inserted into the tubular scaffold 100 so that the scaffold 100 sits on-top and covers the valve. In this way, some part of the tube will be integrated into the frame 600 so that the leaflets 504 are continuously connected to each other and to the base 602 and upstanding posts 604 of the frame 600. This continuous connection will help the leaflets 504 and the valve to have more durability and prevents fatigue on the structure due to improper attachments of leaflets to the base 602 and upstanding posts 604 (as one of the reasons for failure and short term functionality of bioprosthetic heart valves is structural vulnerability and detachment of the leaflets from their base attachment).

After the tubular scaffold is formed into the desired valve shape, it can be used as is or further treated, as desired. As a non-limiting example, the tubular scaffold can be further treated by growing tissue thereon using a mold as described in U.S. application Ser. No. 14/094,760, filed on Dec. 2, 2013, entitled, "Apparatus for Growing a Heart Valve in Three-Dimensions," which is incorporated by reference as though fully set forth herein.

Alternatively and/or in addition to, the formed valve can be implanted with or without surface modification. By using a proper coating method, the valve can become biologically active and recruit the cells inside the body to form a tissue around itself. A method of forming a biological active valve with a mesh scaffold is described in U.S. patent application Ser. No. 13/427,807, filed on Mar. 22, 2012, and entitled. "Mesh Enclosed Tissue Constructs," which is incorporated by reference as though fully set forth herein; however this is not the only method that can be used to form a hybrid biologically active mesh valve. The mesh pattern will help the tissue to have structural integrity from both sides of the mesh. The tissue can be even made before implantation as discussed above. By using cell culture techniques, the tissue can be grown in and around the structure in a way to enclose the mesh.

What is claimed:

1. A tubular scaffold for fabrication of a heart valve, consisting essentially of:
    a tubular mesh material shaped into a valvular structure having at least two leaflets, wherein the tubular mesh material is formed of a layer of mesh having a first side and a second side, the layer of mesh including a network of holes passing directly and unobstructed through the mesh from the first side to the second side; and
    wherein the tubular mesh material is formed of a material such that when pressed into the valvular structure having at least two leaflets and released, the tubular scaffold retains the shape of the valvular structure with the at least two leaflets.

2. The tubular scaffold as set forth in claim 1, wherein the mesh material is braided, such that the tubular mesh material is a tubular braided scaffold.

3. The tubular scaffold as set forth in claim 1, wherein the tubular scaffold is made of polymeric materials.

4. The tubular scaffold as set forth in claim 1, wherein the tubular scaffold is made of metallic materials.

5. The tubular scaffold as set forth in claim 1, wherein the tubular scaffold includes a leaflet portion and a tubular portion, with the leaflets formed on the leaflet portion.

6. The tubular scaffold as set forth in claim 1, wherein a shape of each leaflet corresponds to a portion of a surface of a cone which portion is defined by the intersections on the conical surface of at least two flat planes having peripheries on the conical surface corresponding in length respectively to the circumference of the base with the leaflets each having a peripheral free portion while on the other side are attached to a tubular portion.

7. The tubular scaffold as set forth in claim 1, wherein the tubular scaffold is shaped into a tri-leaflet valvular structure.

8. The tubular scaffold as set forth in claim 1, wherein the tubular scaffold is shaped into a bi-leaflet valvular structure.

9. A tubular scaffold for fabrication of a heart valve, consisting essentially of:
    a tubular mesh material shaded into a valvular structure having at least two leaflets, wherein the tubular mesh material is formed of a layer of mesh having a first side and a second side, the layer of mesh including a network of holes passing directly and unobstructed through the mesh from the first side to the second side; and
    wherein the tubular mesh material is formed of a material such that when pressed into the valvular structure having at least two leaflets and released, the tubular scaffold retains the shape of the valvular structure with the at least two leaflets;
    wherein the tubular mesh material shaped into a valvular structure is fitted onto a frame of an artificial heart valve.

10. A tubular scaffold for fabrication of a heart valve, consisting essentially of:
    a tubular mesh material shaded into a valvular structure having at least two leaflets, wherein the tubular mesh material is formed of a layer of mesh having a first side and a second side, the layer of mesh including a network of holes passing directly and unobstructed through the mesh from the first side to the second side; and
    wherein the tubular mesh material is formed of a material such that when pressed into the valvular structure having at least two leaflets and released, the tubular scaffold retains the shape of the valvular structure with the at least two leaflets;
    wherein the tubular mesh material is connected to a frame having a base and at least two upstanding posts, with the at least two leaflets residing between the at least two posts to form the valvular structure with the at least two leaflets.

* * * * *